(12) United States Patent  
Deterre et al.

(10) Patent No.: US 9,847,739 B2  
(45) Date of Patent: Dec. 19, 2017

(54) AUTONOMOUS INTRACORPOREAL CAPSULE WITH ENERGY HARVESTING BY PIEZOELECTRIC TRANSDUCER

(71) Applicant: SORIN CRM SAS, Clamart (FR)

(72) Inventors: Martin Deterre, Paris (FR); Elie Lefeuvre, Montreuil (FR)

(73) Assignee: Sorin CRM S.A.S., Clamart (FR)

( * ) Notice: Subject to any disclaimer, the term of this patent is extended or adjusted under 35 U.S.C. 154(b) by 572 days.

(21) Appl. No.: 14/499,850

(22) Filed: Sep. 29, 2014

(65) Prior Publication Data

US 2015/0091415 A1    Apr. 2, 2015

(30) Foreign Application Priority Data

Oct. 1, 2013 (FR) ...................... 13 59465

(51) Int. Cl.
| | |
|---|---|
| *H01L 41/113* | (2006.01) |
| *H02N 2/18* | (2006.01) |
| *A61N 1/39* | (2006.01) |
| *A61B 5/00* | (2006.01) |
| *A61N 1/378* | (2006.01) |
| *A61N 1/36* | (2006.01) |

(52) U.S. Cl.
CPC ............ *H02N 2/186* (2013.01); *A61B 5/686* (2013.01); *A61N 1/3785* (2013.01); *A61N 1/3962* (2013.01); *H01L 41/1134* (2013.01); *H01L 41/1136* (2013.01); *A61N 1/36* (2013.01)

(58) Field of Classification Search
CPC .................................. H02N 2/18; A61N 1/378
See application file for complete search history.

(56) References Cited

U.S. PATENT DOCUMENTS

| | | | |
|---|---|---|---|
| 3,456,134 A | 7/1969 | Ko | |
| 5,814,921 A * | 9/1998 | Carroll | F03B 13/16 290/53 |

(Continued)

FOREIGN PATENT DOCUMENTS

| | | |
|---|---|---|
| EP | 2 520 333 | 11/2012 |
| EP | 2 639 845 | 9/2013 |

(Continued)

OTHER PUBLICATIONS

Foreign Search Report for French Patent Application No. FR 1359465, dated Nov. 29, 2013, 2 pages.

*Primary Examiner* — J. San Martin  
(74) *Attorney, Agent, or Firm* — Foley & Lardner LLP (57) ABSTRACT

An autonomous intracorporeal capsule comprises a body containing electronic circuits and an energy harvesting module. The energy harvesting module comprises a moveable surface on the body of the capsule, subjected to pressure variations and to produce a mechanical stress under the effect of the pressure variations, and a transducer comprising a deformable piezoelectric component configured as a beam adapted to be forced to bend. The piezoelectric component has a recessed end integral with the capsule and a free end. A mechanical connection couples the free end of the piezoelectric component to the actuator. The mechanical connection may provide a degree of freedom in rotation between a main direction of the beam and the direction of application of the mechanical stress.

22 Claims, 5 Drawing Sheets

(56) References Cited

U.S. PATENT DOCUMENTS

| | | | | |
|---|---|---|---|---|
| 7,436,104 B2* | 10/2008 | Clingman | ............... | H02N 2/18 310/26 |
| 2001/0035723 A1* | 11/2001 | Pelrine | ............... | F02G 1/043 318/116 |
| 2006/0136004 A1 | 6/2006 | Cowan et al. | | |
| 2006/0202592 A1* | 9/2006 | Ruggeri | ............... | H01L 41/0933 310/349 |
| 2007/0032749 A1* | 2/2007 | Overall | ............... | A61B 5/02444 600/595 |
| 2007/0088397 A1 | 4/2007 | Jacobson | | |
| 2007/0114890 A1* | 5/2007 | Churchill | ............... | H01L 41/1136 310/339 |
| 2007/0145861 A1* | 6/2007 | Tanner | ............... | A45F 3/08 310/339 |
| 2008/0074083 A1* | 3/2008 | Yarger | ............... | H01M 6/5033 320/137 |
| 2009/0015103 A1* | 1/2009 | Rastegar | ............... | F03B 13/20 310/328 |
| 2009/0216292 A1* | 8/2009 | Pless | ............... | A61N 1/3785 607/33 |
| 2009/0281600 A1* | 11/2009 | Lemieux | ............... | H02K 33/18 607/61 |
| 2009/0309458 A1* | 12/2009 | Chou | ............... | H02N 2/18 310/339 |
| 2009/0322184 A1* | 12/2009 | Carman | ............... | H02N 2/186 310/339 |
| 2010/0171394 A1* | 7/2010 | Glenn | ............... | A61N 1/372 310/339 |
| 2010/0317977 A1* | 12/2010 | Piaget | ............... | A61B 5/0031 600/486 |
| 2011/0275947 A1* | 11/2011 | Feldman | ............... | A61N 1/0563 600/508 |
| 2011/0304240 A1* | 12/2011 | Meitav | ............... | A61N 1/3785 310/319 |
| 2012/0074815 A1* | 3/2012 | Jean-Mistral | ............... | H02N 2/18 310/339 |
| 2012/0240672 A1* | 9/2012 | Frey | ............... | H01L 41/053 73/146.5 |
| 2012/0283807 A1* | 11/2012 | Deterre | ............... | A61N 1/3975 607/116 |
| 2012/0286625 A1 | 11/2012 | Cherian | | |
| 2013/0238072 A1* | 9/2013 | Deterre | ............... | H01L 41/0836 607/122 |
| 2013/0238073 A1* | 9/2013 | Makdissi | ............... | A61N 1/36542 607/126 |

FOREIGN PATENT DOCUMENTS

| | | |
|---|---|---|
| WO | WO-2007/047681 A2 | 4/2007 |
| WO | WO-2013/077301 | 5/2013 |
| WO | WO-2013/081560 | 6/2013 |
| WO | WO-2013/121759 | 8/2013 |

* cited by examiner

AUTONOMOUS INTRACORPOREAL CAPSULE WITH ENERGY HARVESTING BY PIEZOELECTRIC TRANSDUCER

CROSS-REFERENCE TO RELATED APPLICATION

This application claims the benefit of and priority to French Patent Application No. 1359465, filed Oct. 1, 2013. French Patent Application No. 1359465 is hereby incorporated by reference in its entirety.

BACKGROUND

The invention is related to the domain of the "medical devices" as defined by the directive 93/42/CE of Jun. 14, 1993 of the European Communities, and notably the "active implantable medical devices" as defined by the directive 90/385/CEE of Jun. 20, 1990 of the European Communities. This definition in particular includes the implants that continuously monitor the cardiac rhythm and deliver if necessary to the heart electrical pulses of stimulation, cardiac resynchronization, cardioversion and/or defibrillation in case of a rhythm disorder detected by the device. It also includes neurological devices, cochlear implants, etc., as well as devices for pH measurement or devices for intracorporeal impedance measurement (such as the measure of the transpulmonary impedance or of the intracardiac impedance).

The invention relates more particularly to those of these devices that implement autonomous implanted capsules and are free from any physical connection to a main implanted (such as the can of a stimulation pulse generator).

These autonomous capsules are called for this reason "leadless capsules" to distinguish them from the electrodes or sensors placed at the distal end of a lead, this lead being traversed throughout its length by one or more conductors connecting by galvanic liaison the electrode or the sensor to a generator connected at the opposite, proximal end, of the lead. Such leadless capsules are for example described in U.S. 2007/0088397 A1 and WO 2007/047681 A2 (Nanostim, Inc.) or in the U.S. 2006/0136004 A1 (EBR Systems, Inc.).

These leadless capsules can be epicardial capsules, fixed to the outer wall of the heart, or endocardial capsules, fixed to the inside wall of a ventricular or atrial cavity, by a protruding anchoring helical screw, axially extending the body of the capsule and designed to penetrate the heart tissue by screwing to the implantation site. The invention is nevertheless not limited to a particular type of capsule, and is equally applicable to any type of leadless capsule, regardless of its functional purpose.

A leadless capsule includes various electronic circuits, sensors, etc., and a transmitter/receiver for wireless communication for remote data exchange. The signal processing inside the capsule and its remote transmission requires a non-negligible energy compared to the energy resources this capsule can store. However, due to its autonomous nature, the capsule can only use its own resources, such as an energy harvester circuit (by the movement of the capsule), associated with an integrated small buffer battery.

The invention relates more particularly to capsules whose energy harvesting uses a mechanic-electric transducer of the piezoelectric type (hereinafter "piezoelectric component") cyclically and alternatively stressed in bending so as to generate electric charges, which charges are then harvested by the self-supply of the capsule system. The mechanical stress of the component can in particular be caused by variations in the pressure of fluid surrounding the capsule (typically, the blood medium), which cyclically deforms or moves a flexible membrane or a mobile surface linked to a bellows (elements designated hereinafter as "actuation element"), this membrane or this surface being connected to the piezoelectric component by a suitable coupling element such as a rod, a strut, etc. (hereinafter "connection element"). EP 2639845 A1 (Sorin CRM) describes such a structure of energy harvesting. Other examples of energy harvesters implementing a piezoelectric component are disclosed by WO 2013/081560 A1, U.S. Pat. No. 3,456,134 A, US 2012/286625 A1, WO 2013/121759 A1 or WO 2013/077301 A1.

Two configurations are possible, depending on the method by which the piezoelectric component is mounted in the casing of the capsule and according to the position of the point of application of the force transmitted by the connection element which stresses the component.

In a first, not symmetrical, configuration the piezoelectric component is blade-shaped or beam-shaped (in the sense of strength of materials) secured to the body of the capsule at one of its ends ("free-clamped" configuration) and is stressed in bending by a force applied to its free opposite end. This configuration allows a maximum deformation of the blade, so a high level of charges is generated and thus provides efficient mechanic-electric conversion. However, the non-symmetrical arrangement of the various elements, in particular of the connection element relative to the body, requires a non-symmetrical displacement of the actuation element and a non-homogeneous deformation of the diaphragm or of the bellows relative to the body of the capsule, which is undesirable for mechanical reliability reasons.

In a second, symmetric, configuration the piezoelectric component is secured to the body at its two ends ("clamped-clamped" configuration) and subjected to bending stress by a force applied to its center. This configuration allows movement of the operation element parallel to itself and therefore a homogeneous deformation of the diaphragm or bellows. However, it does not allow a high amplitude of deformation of the piezoelectric component, said second configuration being more rigid than the first. Typically, for a given dimension of the component, the stiffness of a clamped-clamped configuration is eight times higher than that of a clamped-free configuration, requiring a bending displacement of the component, and thus to eight times less of harvested energy.

To increase flexibility, one must either reduce the thickness of the piezoelectric component (but the limits of this technological solution is quickly reached) or increase its length while maintaining the symmetrical configuration. This solution is proposed by the EP 2 639 845 cited above, which teaches structuring the component with a spiral or coil shape to increase the effective length and flexibility, while maintaining a centered coupling allowing symmetric deformation of the bellows or diaphragm. However, although such structures are very flexible, transduction performance remains relatively low, due to two specific phenomena:

Curved or wound structures are subject to phenomena of torsion, which consequently results in a large part of the mechanical energy applied to the transducer stored as torsion elastic energy, while only the bending energy is converted into electricity; and Mechanical deformations of an elongated and wound structure (even a simple linear structure of the clamped-clamped type) are complex, with curvature inflections. Under stress, the component has zones under tension alternating with zones under compression, creating changes of sign of the electrical potential created by the piezoelectric effect (the more elongated and complex the structure is to increase its flexibility the more changes). This phenomenon can be taken into account by providing the component with charge harvesting electrodes which are separate for each respective zone stressed in tension or compression. However, the structuring of the electrodes adds additional complexity of design and realization of the component, without completely solving the problem of the poor conversion efficiency resulting from the multiplication of sign changes of the electric potential in the piezoelectric material.

SUMMARY

An object of the invention is to overcome these constraints and limitations, by proposing a new type of energy harvester for leadless capsules incorporating a piezoelectric component with high transduction efficiency, to convert in electricity the largest part of an input mechanical energy produced by an actuating element stressed cyclically.

Another object of the invention is to ensure that the stress of the piezoelectric component, which typically results from variations of pressure of the medium such as the blood pressure changes during successive cardiac cycles, is associated with a uniform deformation of the various organs of the actuation element (bellows, membrane, etc.), thereby ensuring mechanical reliability over the long term.

Embodiments of the application include an energy harvester having:
A simple configuration of the free-clamped type, and
Between the actuation element and the free end of the component, a mechanical coupling performed by an organ disposed on the free end and allowing a degree of freedom in pivoting of this free end, so as to allow the transmission of efforts without inflection of component curvature and therefore without reaction effect which would lead to a non-homogeneous deformation of the bellows or diaphragm of the capsule.

More specifically, the invention proposes an autonomous intracorporeal capsule having a body and, inside the body, an electronic circuit and an energy harvesting module for the power supply of the electronic circuits. The energy harvesting module includes an actuation element, a mechanic-electric transducer including at least one deformable piezoelectric component, a connection element coupling the actuation element and the piezoelectric component, and methods for harvesting the electrical charges produced by the piezoelectric component. The actuation element includes a mobile surface of the body of the capsule adapted to be subjected to pressure cyclic changes in the medium surrounding the capsule and to produce a cyclic mechanical stress under the effect of the pressure variations. The connection element transmits to the piezoelectric component, in an application point and according to a direction of application, this mechanical stress and thus cyclically produces bending deformations of the piezoelectric component able to generate electric charges, the piezoelectric component including a straight elongated flexible blade which extends along a main blade direction, perpendicular to the application direction of the mechanical stress.

According to aspects of the invention, the blade is configured as a clamped-free beam adapted to be forced to bend without curvature inversion, with a recessed end integral of the body of the capsule and a free end, at the opposite, connected to the connection element at the point of application of the mechanical stress. A mechanical connection for coupling the free end of the blade to the connection element are further provided, the mechanical connection having a degree of freedom in pivoting between the main direction of the blade and the direction of application of the mechanical stress.

According to various embodiments:
The mechanical connection may include an intermediate element of flexible polymeric material connecting the free end of the blade with the connection element;
The mechanical connection may include a bracket connected to the connection element with two legs arranged on either side of the free end of the blade and a coupling interlayer disposed between each respective leg and the face in vis-à-vis the blade. The coupling interlayer may include, an element of flexible polymer material connecting the leg to the face vis-à-vis the blade, a needle forming a fulcrum of the leg against the face vis-à-vis the blade, or a ball bearing or a roller forming a support bearing assembly of the leg against the face vis-à-vis the screw blade;
The mechanical connection may include a hinge with a ball integral with the free end of the blade, cooperating with a seat formed on the connection element, or vice versa;
The capsule may include an asymmetric structure, wherein the connection element is connected at a central point of the actuation element, or a symmetrical split structure, with two components and two piezoelectric components and two respective connection elements connected to the common actuation element in diametrically opposed points of this actuation element; and
The blade may have a progressively decreasing width from its recessed end towards its free end.

BRIEF DESCRIPTION OF THE FIGURES

Further features, characteristics and advantages of the present invention will become apparent to a person of ordinary skill in the art from the following detailed description of preferred embodiments of the present invention, made with reference to the drawings annexed, in which like reference characters refer to like elements and in which.

DETAILED DESCRIPTION

A structure of a leadless capsule, according to the prior art, will be described with reference to FIGS. 1-8 depicting exemplary embodiments of such a leadless capsule with an energy harvester including a piezoelectric component.

Figure 1:
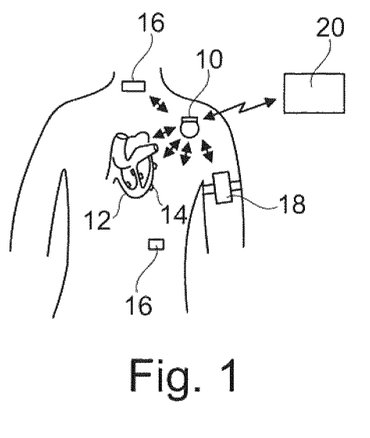
FIG. 1 schematically illustrates a set of medical devices including leadless capsules, implanted within the body of a patient.

In FIG. 1, a set of medical devices implanted within the body of a patient is illustrated. The patient is implanted for example with an implant 10 such as an implantable defibrillator/pacemaker/resynchronizer or a subcutaneous defibrillator or a long-term event recorder. This implantable device 10 is the master device of a network including a plurality of slave devices 12 to 18, which may include intracardiac (12) or epicardial (14) capsules located directly on the patient's heart, other devices such as myopotential sensors or neurological stimulation devices, and optionally an external device 18 disposed on an armband and provided with electrodes in contact with the skin. The device 10 can also be used as a gateway with the external environment to communicate with an external peripheral device 20 such as a programmer or a data remote transmission device with which it communicates by telemetry.

Figure 2:
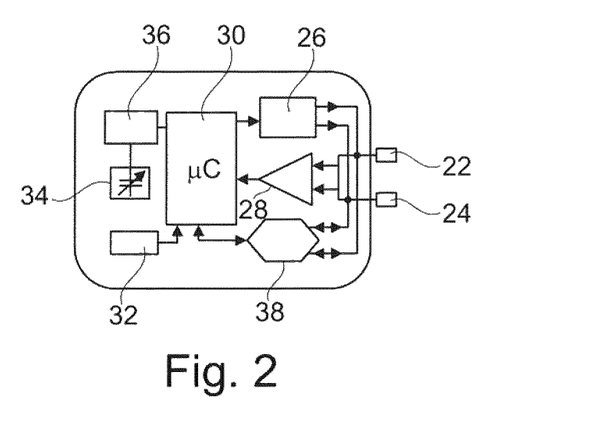
FIG. 2 is a functional block diagram showing the various stages constituting a leadless capsule.

FIG. 2 schematically illustrates the different internal circuit of the implantable autonomous capsules 12-16. The capsule includes for example a pair of electrodes 22, 24 connected to a stimulation pulse generator circuit 26 (for an active capsule incorporating this feature) and/or a detection circuit 28 for the collection of depolarization potential collected between electrodes 22 and 24. A central circuit 30 includes all of the electronics for controlling the various functions of the capsule, for storing the collected signals, etc. It includes a microcontroller and an oscillator generating the clock signals required for the operation of the microcontroller and for the communication. It may also contain an analog/digital converter and a digital storage memory. The capsule may also be provided with a sensor 32 such as an acceleration sensor, a pressure sensor, an hemodynamic sensor, a temperature sensor, an oxygen saturation sensor, etc. The capsule includes an energy harvesting module 34 powering all the circuits via an energy power management stage 36. Electrodes 22 and 24 are also connected to a transmission/reception circuit of pulses 38 used for wireless communication with the master device or other capsules.

Figure 3:
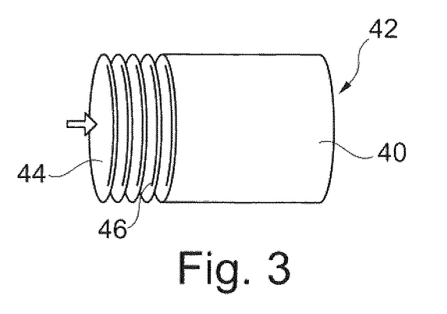
FIGS. 3 and 4 illustrate two possible embodiments of a leadless capsule body with means for harvesting the pressure variations of the surrounding fluid.
Figure 4:
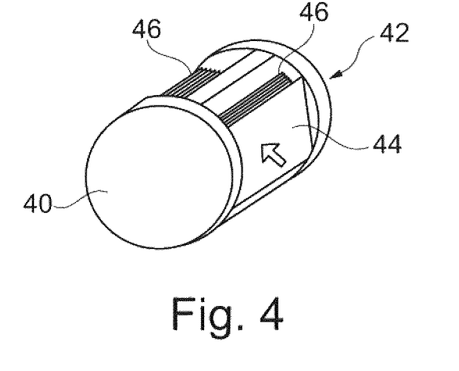

The invention relates particularly to the energy harvesting module 34. The purpose is to harvest the energy contained in the mechanical forces to which the capsule is subjected, typically the blood pressure changes. To take into account pressure variations, the capsule is formed, as shown in FIGS. 3 and 4, provided with a body 40 provided with one or more deformable elements stressed at the rhythm of the pressure variations, with a rigid surface 44 on which the pressure variations are exerted, and which is connected to the body 40 by a deformable portion, such as bellows 46. In the example of FIG. 3, this surface/bellows set 44/46 is disposed on an axial end side of the capsule 40, while in the example of FIG. 4 there are provided two surface/bellows sets 44/46 disposed on lateral sides of the body 40 of the capsule, the rigid surfaces 44 being parallel to each other and to the main axis of the capsule.

The capsule holds, on its face and intended to come into contact with the body wall, an anchoring device 42 (diagrammatically shown in particular in FIGS. 5a and 5b), such as screws or barbs for anchoring the capsule at the location of the chosen implantation site, for example on an inner wall of a cavity of the myocardium.

Figure 5A:
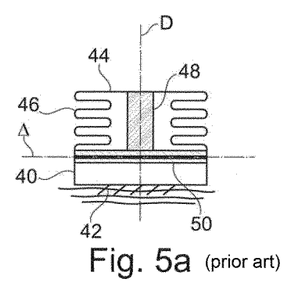
FIGS. 5a, 5b and 5c are views, respectively in section at rest, in section during operation, and a diagrammatic perspective view, of an energy harvester unit with a piezoelectric transducer according to prior art.
Figure 5B:
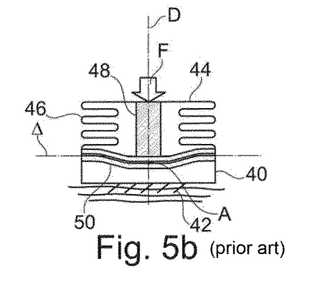
Figure 5C:
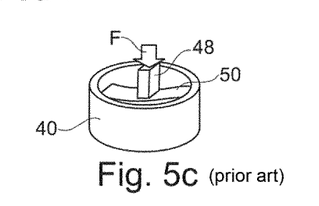

FIGS. 5a to 5c schematically illustrate a configuration of the piezoelectric transducer according to prior art, for a harvester with bellows as illustrated in FIGS. 3 and 4 and disclosed, for example, in EP 2520333 A1 (Sorin CRM). In this embodiment, the external physical force F, resulting from changes in blood pressure on the rigid surface 44, is transmitted via a rod 48 or a connection element analog to component 50 forming a transducer of a piezoelectric type for energy harvesting. This component 50 converts the mechanical force F into electric charges through the direct piezoelectric effect, wherein the mechanical force F transmitted by the connection element 48 generates electric charges collected by the electrodes formed on the surface of the piezoelectric component 50. Electrical energy thus harvested is then processed by the power storage and management module 36.

From the dimensional point of view, the structures of the piezoelectric component used are a few millimeters long, a few hundred micrometers to a few millimeters wide and tens to hundreds of micrometers thick. As regards the material, the piezoelectric layers of the component 50 may be made of a ceramic material such as PZT or single crystal such as PMN-PT, barium titanate, or lithium niobate having a high electromechanical coupling.

In general, the input mechanical energy due to the force of blood pressure is of low intensity, particularly several tens to several hundreds of mN for a displacement of the order of a few hundred microns. This means that the stiffness of the system is low, typically hundreds to thousands of mN/m. To meet this flexibility criterion (low stiffness) while remaining compatible with the requirement of miniaturization, it has been proposed, including in the aforementioned EP 2639845, to conform the component 50 with a band structure folded in a zigzag or in a spiral.

Figure 6:
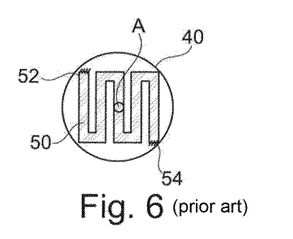
FIGS. 6 and 7 are top views of piezoelectric components formed of wound coil or spiral strips, according to the prior art.
Figure 7:
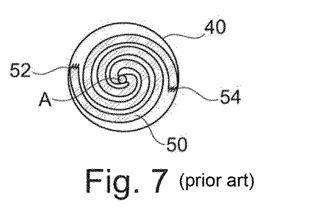

This configuration is illustrated in FIGS. 6 and 7. The strip component 50 is secured to the body 40 of the capsule at both ends 52, 54, so as to obtain a thin and long structure of the type "clamped-clamped" beam, the stress being applied to the central point A. This arrangement extends the length of the piezoelectric structure without losing compactness. However, such a structure has the drawback of experiencing torsion phenomena, which is inherent to rolled or folded configurations. Thus, a significant part of the mechanical energy applied to the input is stored as torsion elastic energy which, unlike the bending energy, is not convertible into electricity, thus degrading the performance of transduction of mechanical energy into electrical energy compared to a component of the straight beam type, which is only subject to bending stresses.

Figure 8:
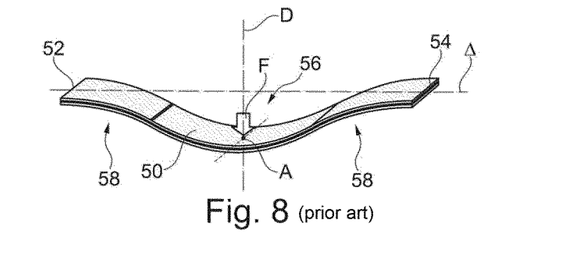
FIG. 8 is a schematic perspective view illustrating the deformations undergone by a piezoelectric component of the clamped-clamped type.

Another drawback of this known configuration is that, as shown in FIG. 8, for a "clamped-clamped" beam structure wherein the piezoelectric component 50 is rigidly secured at its two ends 52, 54 of the capsule body, the deformation of the beam will necessarily cause the formation of a concave central region 56 with on its two sides convex regions 58, or vice versa for a stress in the other direction. This change in curvature is electrically resulting in inversion of the polarity of the charges generated along the beam, requiring electrical isolation of the electrodes according to their concavity. Indeed, to avoid the recombination of charges, the electrodes must be separated on the different regions undergoing different curvatures. It is therefore necessary to structure the electrodes in distinct sets, each generating a different polarity. In the case of rolled or folded structures such as those of FIGS. 6 and 7, these sign changes are multiplied, leading to many sign changes of the generated charges that lead to performance degradation of transduction yield.

We will now describe embodiments of the new invention, with reference to FIGS. 9-15. In these figures, various embodiments configured to increase significantly the conversion efficiency of known devices such as those just described are presented. The basic idea of the invention, unlike in the "clamped-clamped" configurations proposed so far, it to use a simple "clamped-free" configuration with a blade-shaped or straight beam shaped piezoelectric component.

Used as such, this type of "clamped-free" structure has the mechanical drawback, due to the reaction effects between the piezoelectric component and the actuation element, to lead to a displacement of the actuation element not parallel to itself. This, therefore, may lead to an inhomogeneous deformation of the bellows (which would crush more at the free end than at the recessed end of the component), causing significant mechanical reliability problems of the structure in the long-term.

Figure 9A:
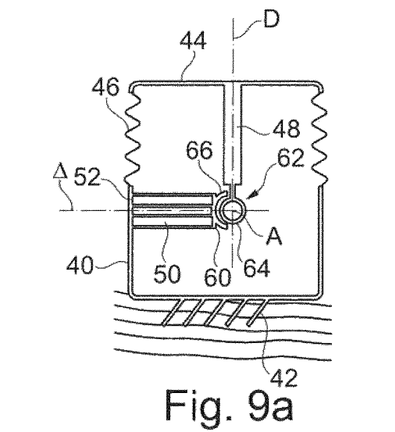
FIGS. 9a, 9b and 9c are sectional views, respectively at rest, in operation with a stress in one direction and in operation with a stress in the opposite direction, of an energy harvesting system according to a first embodiment of the invention.
Figure 9B:
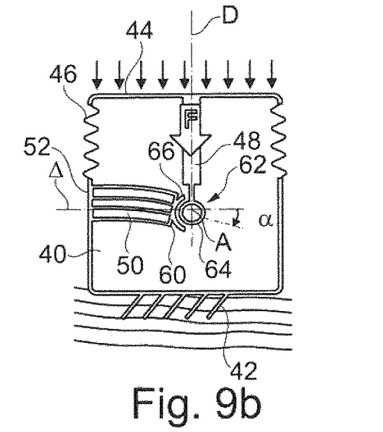
Figure 9C:
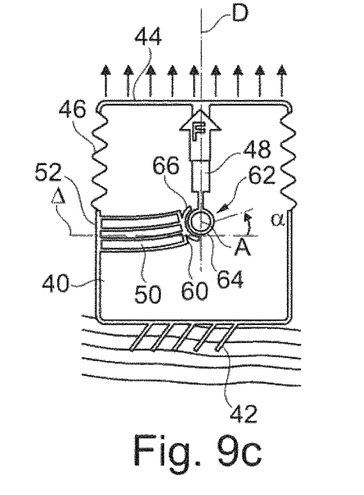

To avoid this, and to allow a homogeneous and symmetric deformation of the bellows, the invention proposes, as can be seen in particular in FIG. 9a, to make a mechanical connection of the pivot type 62 between an actuator and the free end 60 of the deformable piezoelectric component. In a preferred embodiment, the actuator comprises the connection element 48 linked to the actuation element 44 receiving the efforts and transmitting the efforts in the direction D forming an axis of symmetry of the bellows 46 thereof. Thus, such a system does not affect the deformation of the bellows 46 or the displacement of the actuation element 44, which can move parallel to itself respectively in one direction or in the other depending on the positive or negative variations of the surrounding pressure, as illustrated in FIGS. 9b and 9c.

The piezoelectric component 50 may bend in one direction or in the other (FIGS. 9b and 9c) on both sides of its equilibrium position (FIG. 9a) corresponding to the main direction Δ along which the component extends. These movements will not transmit torsional forces to the connection element 48, efforts which could affect, by reaction, the movement of the actuation element 44 and hence the deformation of the bellows 46.

This is achieved by the degree of freedom in rotation (angle α in FIGS. 9b and 9c), allowed by the mechanical connection of the pivot type 62 between the free end 60 of the component 50 and the connection element 48. In FIGS. 9a to 9c, this connection has been illustrated in the form of a ball 64 integral with the connection element 48 and cooperating with a seat 66 integral with the free end 60 of the piezoelectric component 50.

This configuration has several advantages: First, relative to a "clamped-clamped" (as in FIG. 8) configuration, the "clamped-free" configuration has a stiffness eight times lower which allows, for an inputted given force F (the value of which is imposed by the significance of changes in blood pressure and by the area of the mobile surface 44) to increase eight times the amplitude of displacement and thus the harvestable energy. Secondly, the "clamped-free" proposed structure has only one type of mechanical stress by piezoelectric layer, due to the lack of inversion of curvature: only voltage on one side, and only compression on the opposite side. Thus, a simple unstructured electrode is sufficient to harvest energy, which frees manufacturing of a patterning step of the electrodes. Furthermore this configuration generates a much greater amount of charges and, thus, energy. The yield of the piezoelectric transducer is therefore much higher than conventional structures of the prior art. And finally, a "clamped-clamped" configuration, in addition to having eight times higher stiffness than that of a "clamped-free" configuration, very quickly takes on a nonlinear behavior (as soon as the movement is about half the thickness of the beam), making this configuration more rigid.

Figure 10:
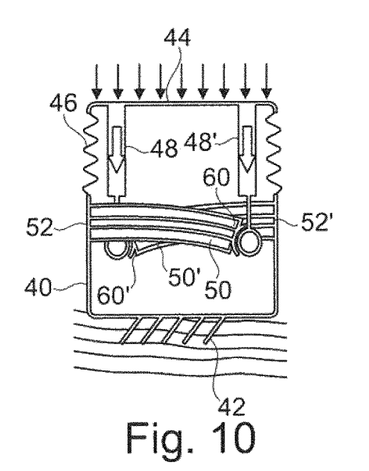
FIG. 10 is the counterpart of FIG. 9b, for a variant of the first embodiment with duplication of the piezoelectric transducer.

FIG. 10 illustrates a configuration in which the piezoelectric component 50 occupies the maximum diametrically permitted length in the body 40. Indeed, it may be useful to maximize the blade length of the component 50 to reduce its stiffness. In this case, to ensure a symmetrical deformation of the bellows 46, two identical transducers 50, 50', having a upside-down configuration, symmetrical to the center of the capsule, are provided. Each transducer 50, 50' has a recessed fixed end 52, 52' and a free end 60, 60' which is connected to a respective connection element 48, 48' connected to the common actuation element 44 at two diametrically opposite points thereof. The recessed ends 52, 52' are also located at two diametrically opposite sides of the capsule body 40, so that the forces applied on the respective free ends 60, 60' are symmetrical with respect to the central axis of the capsule. The sum of the two forces is therefore centered, resulting in a symmetrical deformation of the bellows 46.

The configuration of FIG. 10 provides i) nearly double the length of each component 50, 50' and ii) duplication in the number of components. Therefore, in comparison with the configuration of FIG. 9b, FIG. 10 (with the piezoelectric component 50, 50' of the same section) increases the flexibility by a factor of four. Thus, the displacement will be four times greater for a given force (and therefore a given pressure variation), which also gives four times greater energy. Finally, between the structure of the prior art such as that illustrated in FIG. 8 and the structure of the invention with dual component such as that illustrated in FIG. 10, the power supplied is increased by a factor thirty-two.

Figure 11A:
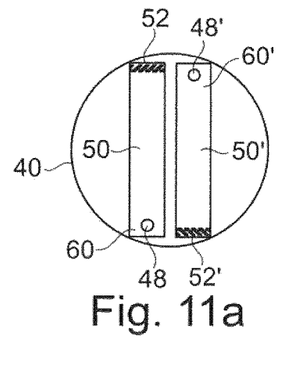
FIGS. 11a, 11b and 11c are top views of various possible shapes of a split piezoelectric component, usable in particular with the embodiment of FIG. 10.
Figure 11B:
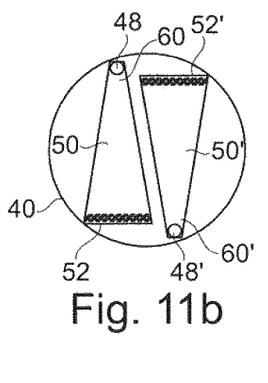
Figure 11C:
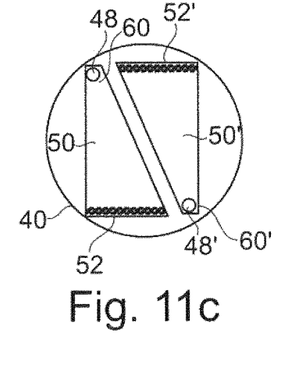

The plan views of FIGS. 11a, 11b and 11c show three possible respective variants of optimization of the shape of the beams of the configuration of FIG. 10, with components 50, 50' of constant width (FIG. 11a) or of variable, decreasing from the fixed clamped end 52, 52' to the free end 60, 60' width (FIGS. 11b and 11c).

Figure 12A:
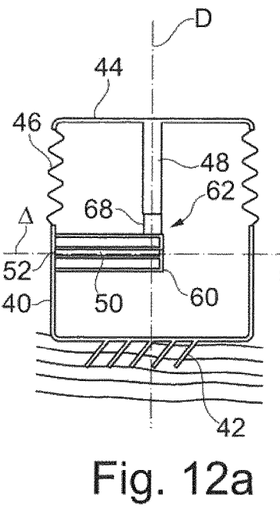
FIGS. 12a, 12b and 12c are counterparts of FIGS. 9a, 9b and 9c, for a second embodiment of the invention.
Figure 12B:
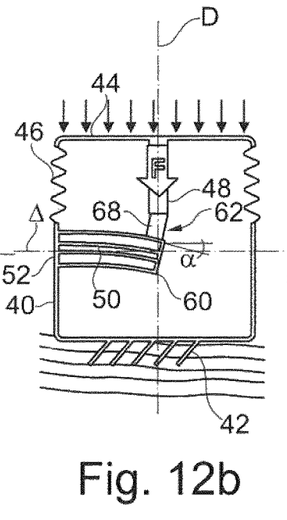
Figure 12C:
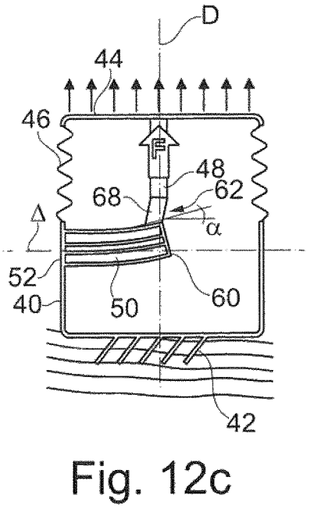

FIGS. 12a to 12c are counterparts of FIGS. 9a to 9c for a particularly advantageous embodiment of the pivot connection 62. In this embodiment, the connection is made from a single deformable element, such as a flexible polymer 68 interconnecting the free end 60 of the component 50 and the end of the connection element 48. The polymer 68 may be a silicone, in particular based on PDMS (polydimethylsiloxane), PEEK (polyetheretherketone), or parylene (poly (p-xylylene)). When the actuation element 44 is lowered (FIG. 12b) the polymer 68 compresses and flexes; conversely, for a movement in the opposite direction (FIG. 12c) the polymer lengthens and absorbs the angular deformation of the free end 60 of the piezoelectric component 50. During these movements, the contact surface between the polymer 68 and the free end 60 of the piezoelectric component 50 is not horizontal and forms a non-zero angle α relative to the main direction Δ of the component 50. This angle allows the arcuate deformation of the component 50 as in the case previously described in FIGS. 9a-9c, with the advantage that the flexible element 68 eliminates any mechanical friction.

Figure 13A:
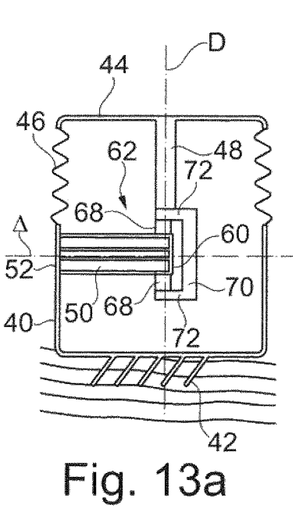
FIGS. 13a, 13b and 13c are counterparts of FIGS. 9a, 9b and 9c, for a third embodiment of the invention.
Figure 13B:
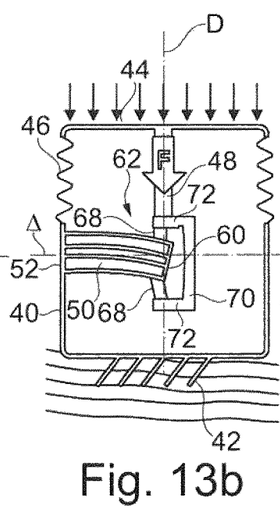
Figure 13C:
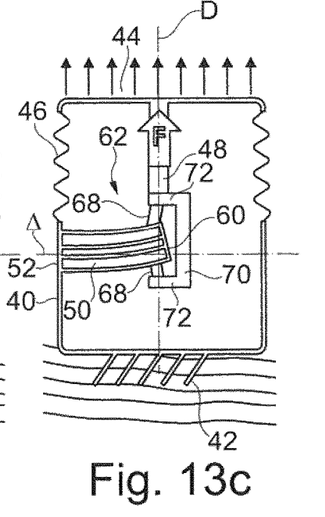

It is possible according to the same principle, as shown in FIGS. 13a to 13c, to have two such flexible polymer elements 68 on each side of the free end 60 of the component 50, one of the elements being located on the upper surface of the component and the other in line with the first, but on the lower surface. These two polymer elements 68 are connected to the two arms 72 of a bracket 70, itself attached to the connection element 48. When the actuation element 44 is lowered (FIG. 13b), the two polymer elements 68 are deformed. The upper surface behaves as in the case of FIG. 12b in compression mode, while the lower one behaves in elongation mode, symmetrically, to allow pivoting of the free end 60 relative to the direction D of application of the force F. In the reverse movement (FIG. 13c), the roles of the two polymer elements 68 are reversed, thereby generally have a homogeneous behavior of the material of these elements for the two directions of displacement.

Figure 14A:
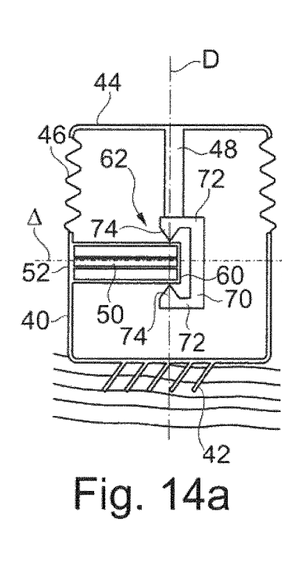
FIGS. 14a, 14b and 14c are counterparts of FIGS. 9a, 9b and 9c, for a fourth embodiment of the invention.
Figure 14B:
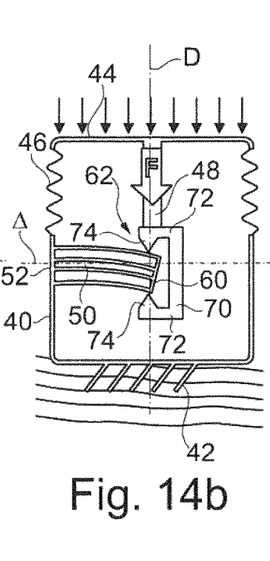
Figure 14C:
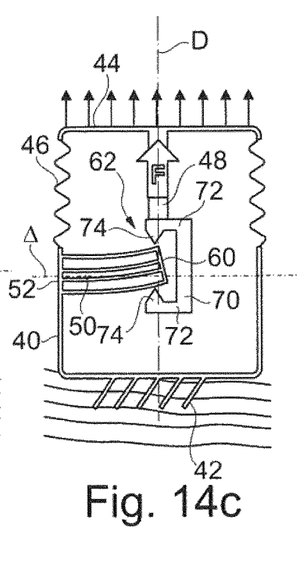

FIGS. 14a to 14c are counterparts of FIGS. 13a to 13c for another embodiment of the pivot connection 62. In this case, the coupling consists of a simple mechanical contact by a pin 74 or an analogous element provided on each of the arms 72 of the bracket 70 and bearing on the component 50 on either side of the free end 60. This end can be, depending on the direction of movement of the connection element 48, push (FIG. 14b) or pull (FIG. 14c).

Figure 15A:
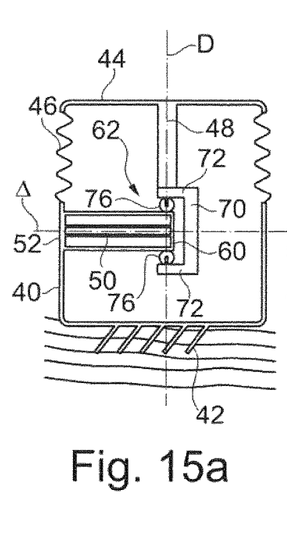
FIGS. 15a, 15b and 15c are counterparts of FIGS. 9a, 9b and 9c, for the fifth embodiment of the invention.
Figure 15B:
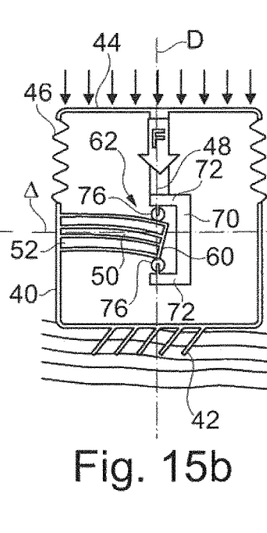
Figure 15C:
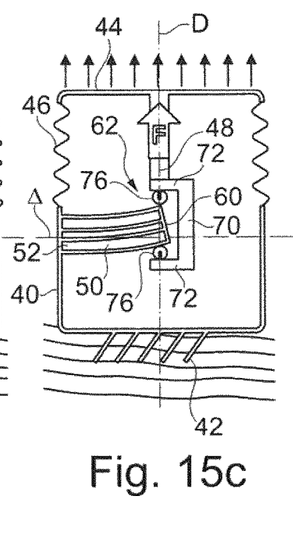

FIGS. 15a to 15c are counterparts of FIGS. 13a to 13c for yet another embodiment of the pivot connection 62. This embodiment is to implement a rolling ball or roller 76 between each face of the component and the branch 72 facing the bracket 70. Thus, during displacement of the actuation element in one direction or in the other (FIGS. 15b and 15c), the mechanism including these rolling balls stoops or raises and moves on the surface of the component 50 along its main direction Δ, allowing the free end 60 to bow and to form an angle without curvature inflexion and thus with a homogeneous charge polarity on the same surface of the piezoelectric component 50.

The invention claimed is:

1. An autonomous intracorporeal capsule comprising:
a body containing therein electronic circuits and an energy harvesting module for supplying power to the electronic circuitry;
the energy harvesting module comprising:
an actuator comprising a moveable surface on the body of the capsule;
a transducer comprising at least a deformable piezoelectric component provided as a beam forced to bend, with a recessed end integral with the body of the capsule and a free end; and
a mechanical connection coupling the free end of the piezoelectric component to the actuator, wherein the mechanical connection provides a degree of freedom in rotation between a main direction of the beam and the direction of application of the mechanical stress.

2. The capsule of claim 1, wherein the deformable piezoelectric component is configured such that when forced to bend, it will bend without inversion of curvature.

3. The capsule of claim 1, wherein the piezoelectric component comprises a rectilinear elongate flexible blade extending along a main direction of blade.

4. The capsule of claim 1, wherein the actuator transmits the mechanical stress to the piezoelectric component at an application point and along a direction of application, and wherein the piezoelectric component beam comprises a rectilinear elongate flexible blade extending along the main direction of blade perpendicular to the direction of application of the mechanical stress.

5. The capsule of claim 1, wherein the mechanical connection comprises a pivot between the free end of the beam and the actuator.

6. The capsule of claim 1, wherein the mechanical connection comprises an intermediate element of flexible polymer material connecting the free end of the beam with the actuator.

7. The capsule of claim 1, wherein the mechanical connection comprises a bracket connected to the actuator with two legs arranged on either side of the free end of the beam and a coupling interlayer disposed between each respective leg and a respective surface of the beam.

8. The capsule of claim 7, wherein the coupling interlayer comprises an element of flexible polymer material connecting the leg to the surface the beam.

9. The capsule of claim 7, wherein the coupling interlayer comprises a pin fulcrum of the leg against the surface of the beam.

10. The capsule of claim 7, wherein the coupling interlayer comprises a ball bearing or a roller forming a support of the leg against the surface of the beam.

11. The capsule of claim 1, wherein the mechanical connection comprises a hinge with a ball integral with the free end of the beam, interacting with a seat formed on the actuator, or vice versa.

12. The capsule of claim 1, comprising an asymmetric structure, wherein a connection element is connected at a central point of the actuator surface and extends between the actuator surface and the mechanical connection.

13. The capsule of claim 1, comprising a symmetrical structure with two piezoelectric components and two respective connection elements connected to the common actuation element in diametrically opposed points of the actuator surface and extending between the actuator surface and respective mechanical connections.

14. The capsule of claim 1, wherein the beam has a progressively decreasing width from its recessed end towards its free end.

15. An energy harvesting module contained in a body, comprising:
a deformable piezoelectric component having a first end coupled to the body and a second end that is a free end;
a connection element extending between the free end of the piezoelectric component and a surface on the body, wherein the connection element applies a mechanical stress produced by pressure variations on the surface of the body to the piezoelectric component, thereby producing bending deformations of the piezoelectric component to generate electric charges;
a mechanical connection coupling the free end of the piezoelectric component to the connection element, the mechanical connection providing a degree of freedom in rotation between the main direction of the piezoelectric component and the direction of application of the mechanical stress.

16. The energy harvesting module of claim 15, wherein the main direction of the piezoelectric component is perpendicular to the direction of application of the mechanical stress.

17. The energy harvesting module of claim 15, wherein the mechanical connection comprises an intermediate element of flexible polymer material connecting the free end of the piezoelectric component with the connection element.

18. The energy harvesting module of claim 15, wherein the mechanical connection comprises a bracket connected to the connection element with two legs arranged on either side of the free end of the piezoelectric component and a coupling interlayer disposed between each respective leg and a respective surface of the piezoelectric component.

19. The energy harvesting module of claim 15, wherein the mechanical connection comprises a hinge with a ball integral with the free end of the piezoelectric component, interacting with a seat formed on the connection element, or vice versa.

20. A method for harvesting energy in an implantable device, comprising:
receiving an external stress on a moveable surface of a body of the implantable device, generating a mechanical force;
transmitting the mechanical force through a connection element to a piezoelectric component, wherein the connection element is coupled between the moveable surface and the piezoelectric component, wherein the piezoelectric component has a first end rigidly coupled to the body of the implantable device and an opposite free end, and wherein the connection element and the piezoelectric component are coupled at a mechanical connection providing a degree of freedom in rotation between a main direction of the piezoelectric component and the direction of application of the mechanical force;
producing bending deformations of the piezoelectric component, by transmitting the mechanical force to the free end via the connection element, to generate electric charges; and
harvesting energy produced by the bending deformations of the piezoelectric component.

21. The method of claim 20, wherein the mechanical force is transmitted by the connection element in a direction perpendicular to the main direction in which the piezoelectric component extends.

22. The method of claim 20, wherein the external stress is transmitted to two piezoelectric components by two respective connection elements connected to the common moveable surface in diametrically opposed points on the moveable surface.

* * * * *